United States Patent [19]

Bellussi et al.

[11] Patent Number: 5,149,896
[45] Date of Patent: Sep. 22, 1992

[54] PROCESS FOR OLIGOMERIZING LIGHT OLEFINS

[75] Inventors: Giuseppe Bellussi, Piacenza; Fabrizio Cavani, Modena; Virginio Arrigoni; Roberto Ghezzi, both of Milan, all of Italy

[73] Assignee: Eniricerche S.p.A., Milan, Italy

[21] Appl. No.: 715,786

[22] Filed: Jun. 14, 1991

[30] Foreign Application Priority Data

Jun. 22, 1990 [IT] Italy ................... 20744 A/90

[51] Int. Cl.$^5$ .............................................. C10L 1/16
[52] U.S. Cl. ............................. 585/532; 585/520
[58] Field of Search ........................ 585/520, 532

[56] References Cited

U.S. PATENT DOCUMENTS

| | | | |
|---|---|---|---|
| 2,145,576 | 1/1939 | Atwell | 585/520 |
| 3,188,360 | 6/1965 | Gudelis | 585/533 |
| 4,335,022 | 6/1982 | Slaugh | 585/532 |
| 4,544,791 | 10/1985 | Juguin et al. | 585/517 |

FOREIGN PATENT DOCUMENTS

| | | |
|---|---|---|
| 0340868 | 11/1989 | European Pat. Off. |
| 766151 | 7/1954 | Fed. Rep. of Germany |
| 0824543 | 12/1959 | United Kingdom |

Primary Examiner—Patrick P. Garvin
Assistant Examiner—E. D. Irzinski
Attorney, Agent, or Firm—Shea & Gould

[57] ABSTRACT

A process for oligomerizing propylene is described, consisting of reacting said olefin in the presence of an X-ray amorphous alumina-silica gel catalyst with a silica/alumina molar ratio of between 30/1 and 500/1, a surface area of between 500 and 1000 m$^2$/g, a total pore volume of between 0.3 and 0.6 ml/g, an average pore diameter of the order of 10 Å or less, and free or substantially free of pores with a diameter greater than 30 Å.

11 Claims, No Drawings

PROCESS FOR OLIGOMERIZING LIGHT OLEFINS

This invention relates to a process for oligomerizing propylene by means of a particular porous amorphous synthetic material. Various processes for olefin oligomerization are known using synthetic zeolites or non-zeolite materials as catalyst. U.S. Pat. No. 3,960,978, EP 31675 and U.S. Pat. No. 4,150,062 for example describe processes for producing gasolines by oligomerization of olefins in the presence of ZSM-5 zeolites. The gasolines obtained also contain an aromatic hydrocarbon fraction. These substances, and in particular benzene, are undesirable because of their noxiousness to man and the environment. U.S. Pat. Nos. 4,227,992; 4,456,779; and 4,720,600 describe oligomerization processes for light olefins catalyzed by ZSM-5 zeolites which by operating at a temperature of at least 250° C. enable products to be obtained containing a hydrocarbon fraction usable as diesel engine fuel. Currently, from an industrial viewpoint, the catalyst most widely used for olefin oligomerization is phosphoric acid supported on silica. The preparation and use of this catalyst are described for example in U.S. Pat. Nos. 2,694,686; 2,833,727; 2,913,506; and 3,661,801.

This catalyst does not require reaction temperatures as high as processes using a zeolite catalyst, but has numerous other drawbacks. It is corrosive, during use it degrades to clog the catalyst bed, with consequent difficulties in discharging the catalyst from the reactor, and when spent it cannot be regenerated and has to be eliminated, with considerable ecological problems connected with its disposal.

Patent application EU Public. No. 0 340.868 described an alumina-silica gel amorphous to X-rays, with a silica/alumina molar ratio of between 30/1 and 500/1, a surface area of between 500 and 1000 m²/g, a total pore volume of between 0.3 and 0.6 ml/g, an average pore diameter of the order of 10 Å or less, and free or substantially free of pores with a diameter greater than 30 Å.

We have now found that it is possible to use this microporous amorphous alumina-silica gel of large surface area and narrow pore diameter distribution as a catalyst in the oligomerization of propylene. This catalyst has none of the aforesaid drawbacks of phosphoric acid on silica, and indeed can be easily regenerated by heat treatment, by which it completely reacquires its activity. When propylene oligomerization is conducted in the presence of this catalyst a product is obtained containing a gasoline fraction (B.P. between 80° and 175° C.) of high octane number and a higher molecular weight hydrocarbon fraction (B.P. between 175° and 360° C.).

The reaction temperature is much lower than that required for zeolite catalysts in producing gasoil from light olefins and in addition the product obtained by the process of the present invention does not contain aromatic hydrocarbons.

We have thus found a process for oligomerizing propylene consisting of reacting it in the presence of an X-ray amorphous alumina-silica gel with a silica/alumina molar ratio of between 30/1 and 500/1, a surface area of between 500 and 1000 m²/g, a total pore volume of between 0.3 and 0.6 ml/g, an average pore diameter of the order of 10 Å or less, and free or substantially free of pores with a diameter greater than 30 Å.

The alumina-silica gel, used as catalyst, can either be used as such or be mixed with suitable metal oxides acting as diluents. Oxides suitable for the purpose include aluminas, silicas and titanium and magnesium oxides. The silica gel and the diluent can be mixed in a weight ratio of between 50/50 and 95/5, and preferably between 70/30 and 90/10.

The two components can be mixed by conventional methods and the mixture be conveniently consolidated into the desired final form, for example in the form of extrudates or granulates.

The oligomerization reaction is conducted preferably continuously in a flow reactor of fixed or fluidized bed, at a temperature of between 100° and 250° C., preferably between 120° and 200° C., at a pressure of between 10 and 70 atm for a contact time of between 5 and 90 minutes.

The propylene can be used either pure, mixed with other olefins or diluted with paraffins.

EXAMPLE 1

Catalyst Preparation 2 g of aluminium isopropylate are dissolved at ambient temperature in 34 g of a 30.6% aqueous solution of tetrapropylammonium hydroxide (TPA-OH). The solution obtained is diluted with 162 g of demineralized water, heated to 60° C. and 104 g of tetraethylsilicate added. The resultant mixture has the following molar ratios:

$SiO_2/Al_2O_3 = 100$ $TPA\text{-}OH/SiO_2 = 0.1$ $H_2O/SiO_2 = 21$

This mixture is kept stirring at 60° C. for 30 minutes until a homogeneous gel is obtained, this then being dried in an air stream at 90° C. and calcined at 550° C. firstly in a nitrogen stream for 3 hours and then in an air stream for 10 hours. 30 g of alumina-silica gel are obtained, with a quantitative yield on the initially fed silicon and aluminium, the gel then being granulated into particles of 1–2 mm. The product has the following characteristics:

$SiO_2/Al_2O_3$ molar ratio = 100/1 surface area = 800 m²/g (measured by a Carlo Erba Sorptomatic 1800 apparatus)

porosity = 0.44 ml/g, average pore diameter about 10 Å, and absence of pores with a diameter exceeding 30 Å (values determined by the Carlo Erba Sorptomatic 1800).

EXAMPLE 2

7.1 g (10 ml) of alumina-silica gel catalyst prepared as described in Example 1 are fed into a steel flow reactor of 15 mm internal diameter heated by a furnace. Propylene is fed in under the following operating conditions:
inlet temperature: 150° C.
hot point temperature: 163° C.
pressure: 30 atm (gauge)
contact time: 21 min The reaction products were analyzed by gas chromatography, giving the following results:
propylene conversion: 70%
selectivity towards:

light hydrocarbons (up to $C_8$): 11.6%
nonenes: 25.1%
heavy hydrocarbons ($C_9+$): 63.3%

After 140 hours of reaction the following results are obtained:
propylene conversion: 51%
selectivity towards:
light hydrocarbons (up to $C_8$): 9.2%
nonenes: 27.1%
heavy hydrocarbons ($C_9+$): 63.7%

The product fraction containing hydrocarbons up to 9 carbon atoms is a high quality gasoline with Octane Number (Research)=96 and Octane Number (Motor)=84.

EXAMPLE 3

7.1 g (10 ml) of alumina-silica gel catalyst prepared as described in Example 1 are fed into a steel flow reactor of 15 mm internal diameter heated by a furnace. Propylene is fed in under the following operating conditions:
inlet temperature: 120° C.
hot point temperature: 127° C.
pressure: 30 atm (gauge)
contact time: 41 min The reaction products were analyzed by gas chromatography, giving the following results:
propylene conversion: 77%
selectivity towards:
light hydrocarbons (up to $C_8$): 8.1%
nonenes: 36.4%
heavy hydrocarbons ($C_9+$): 55.5%

EXAMPLE 4

Comparative 8.3 g (10 ml) of phosphoric acid-on-silica catalyst in the form of extrudates of 6.5 mm length and 5 mm diameter, prepared as described in Example 3 of GB 863,539, are fed into the reactor of the previous example. Propylene is fed under the following operating conditions:
inlet temperature: 150° C.
hot point temperature: 154° C.
pressure: 30 atm (gauge)
contact time: 17 min The reaction products were analyzed by gas chromatography, giving the following results:
propylene conversion: 48%
selectivity towards:
light hydrocarbons (up to $C_8$): 4.3%
nonenes: 48.0%
heavy hydrocarbons ($C_9+$): 47.7%

This performance remains constant for at least 100 hours of reaction.

It can be seen that the activity of the alumina-silica gel catalyst is superior, especially at the commencement of its life, to that of the traditional phosphoric acid-on-silica catalyst.

EXAMPLE 5

This example uses the same catalyst as Example 2 after having regenerated it by heating it in air to 500° C. for 7 hours (heating gradient 50° C./hour). 7.1 g (10 ml) of this regenerated catalyst are loaded into a steel flow reactor of 15 mm internal diameter heated by a furnace. Propylene is fed in under the following operating conditions:
inlet temperature: 150° C.
hot point temperature: 163° C.
pressure: 30 atm (gauge)
contact time: 21 min The reaction products were analyzed by gas chromatography, giving the following results:
propylene conversion: 63%
selectivity towards:
light hydrocarbons (up to $C_8$): 9.6%
nonenes: 22.8%
heavy hydrocarbons ($C_9+$): 67.6%

After 180 hours of reaction the following results are obtained:
propylene conversion: 51%
selectivity towards:
light hydrocarbons (up to $C_8$): 13.4%
nonenes: 25.0%
heavy hydrocarbons ($C_9+$): 61.6%

These data show that the performance of the alumina-silica gel catalyst can be restored by thermal regeneration.

We claim:

1. A process for oligomerizing propylene consisting of reacting olefin comprising propylene by means of an X-ray amorphous alumina-silica gel catalyst with a silica/alumina molar ratio of between 30/1 and 500/1, a surface area of between 500 and 1000 m$^2$/g, a total pore volume of between 0.3 and 0.6 ml/g, an average pore diameter of the order of 10 A or less, and free or substantially free of pores with a diameter greater than 30 A wherein the reaction is conducted at a temperature of between 100° C. and 250° C., at a pressure of between 10 and 70 atm, and for a time of between 5 and 90 minutes.

2. A process as claimed in claim 1, wherein the reaction is conducted at a temperature of between 120° C. and 200° C.

3. A process as claimed in claim 1, wherein the alumina-silica gel catalyst is used in mixture with metal oxides chosen from aluminas, silicas and titanium and magnesium oxides, with a weight ratio of alumina-silica gel to metal oxide between 50/50 and 95/5.

4. A process as claimed in claim 1, wherein the reaction is conducted at a temperature of between 120°-150° C.

5. A process as claimed in claim 1, wherein the pressure is about 30 atm.

6. A process as claimed in claim 1, wherein the reaction time is from about 20 to about 40 minutes.

7. A process as claimed in claim 3, wherein the weight ratio of alumina-silica gel to metal oxide is between 70/30 and 90/10.

8. A process as claimed in claim 1, wherein the product comprises less than about 13.5% light hydrocarbons containing up to 8 carbon atoms.

9. A process as claimed in claim 1, wherein the product comprises at least about 87.5% heavy hydrocarbons containing at least 9 carbon atoms.

10. A process as claimed in claim 9, wherein the product comprises at least about 23% nonene.

11. A process according to claim 9, wherein the product comprises at least about 55% heavy hydrocarbons containing more than 9 carbon atoms.

* * * * *